US010245387B2

(12) United States Patent
Stefanov et al.

(10) Patent No.: US 10,245,387 B2
(45) Date of Patent: Apr. 2, 2019

(54) MEDICAMENT DELIVERY DEVICE

(71) Applicant: CAREBAY EUROPE LTD., Sliema (MT)

(72) Inventors: Slobodan Stefanov, Deerfield Beach, FL (US); Thad Miley, Boca Raton, FL (US)

(73) Assignee: SHL MEDICAL AG, Zug (CH)

( * ) Notice: Subject to any disclaimer, the term of this patent is extended or adjusted under 35 U.S.C. 154(b) by 279 days.

(21) Appl. No.: 15/207,871

(22) Filed: Jul. 12, 2016

(65) Prior Publication Data

US 2018/0015228 A1 Jan. 18, 2018

(51) Int. Cl.
*A61M 5/315* (2006.01)
*A61M 5/20* (2006.01)
*A61M 5/24* (2006.01)

(52) U.S. Cl.
CPC .......... *A61M 5/31595* (2013.01); *A61M 5/20* (2013.01); *A61M 5/24* (2013.01); *A61M 5/31513* (2013.01); *A61M 5/31536* (2013.01); *A61M 5/31551* (2013.01); *A61M 5/31585* (2013.01); *A61M 5/31593* (2013.01); *A61M 5/31511* (2013.01); *A61M 5/31528* (2013.01); *A61M 5/31541* (2013.01); *A61M 2205/581* (2013.01); *A61M 2205/582* (2013.01)

(58) Field of Classification Search
CPC ................ A61M 5/31595; A61M 5/24; A61M 5/31536; A61M 5/31551; A61M 5/31585; A61M 5/31593
See application file for complete search history.

(56) References Cited

FOREIGN PATENT DOCUMENTS

WO  2014/108551 A1  7/2014
WO  WO 2014166735 A1 * 10/2014  ........ A61M 5/31511

* cited by examiner

*Primary Examiner* — Nathan R Price
*Assistant Examiner* — Melissa A Snyder
(74) *Attorney, Agent, or Firm* — McDonnell Boehnen Hulbert & Berghoff LLP

(57) ABSTRACT

A multi-dose medicament delivery device is presented having a housing, a medicament container assembly, a dose drum, a plunger rod, and an activation assembly. The dose drum is supported in the housing via a threaded connection, wherein the dose drum is axially movable with respect to the housing in a backward direction from an initial position to at least one dosing position when rotated in a first direction in order to set a dose to be delivered, and axially movable with respect to the housing in a forward direction from said dosing position to the initial position when rotated in a second, opposite direction in order to deliver the dose set. The plunger rod is operationally associated with the stopper and supported in the housing via a threaded connection, wherein the threaded connection is configured to axially guide the plunger rod toward the device front end when the plunger rod is rotated in the second direction.

17 Claims, 7 Drawing Sheets

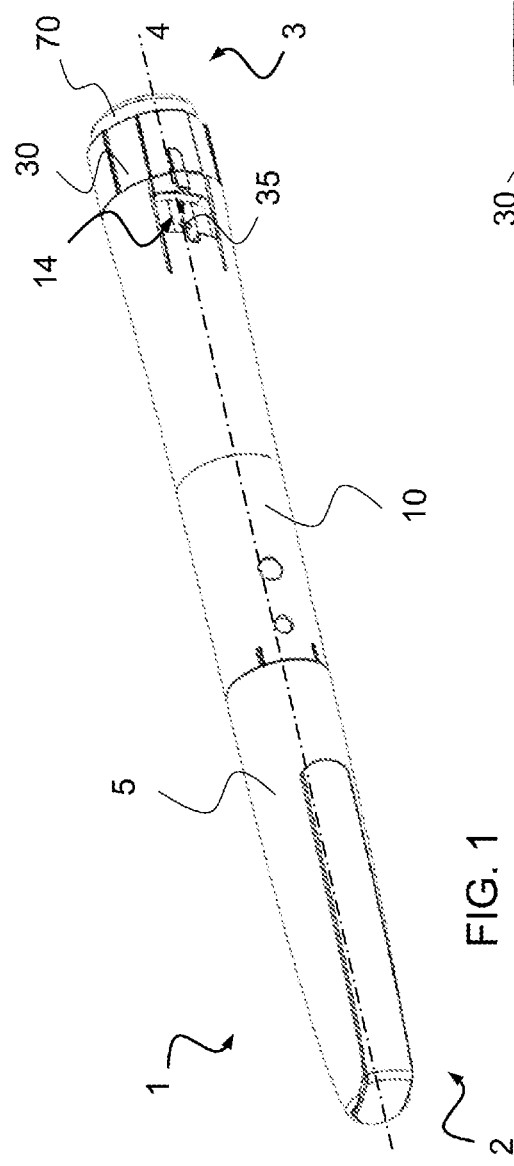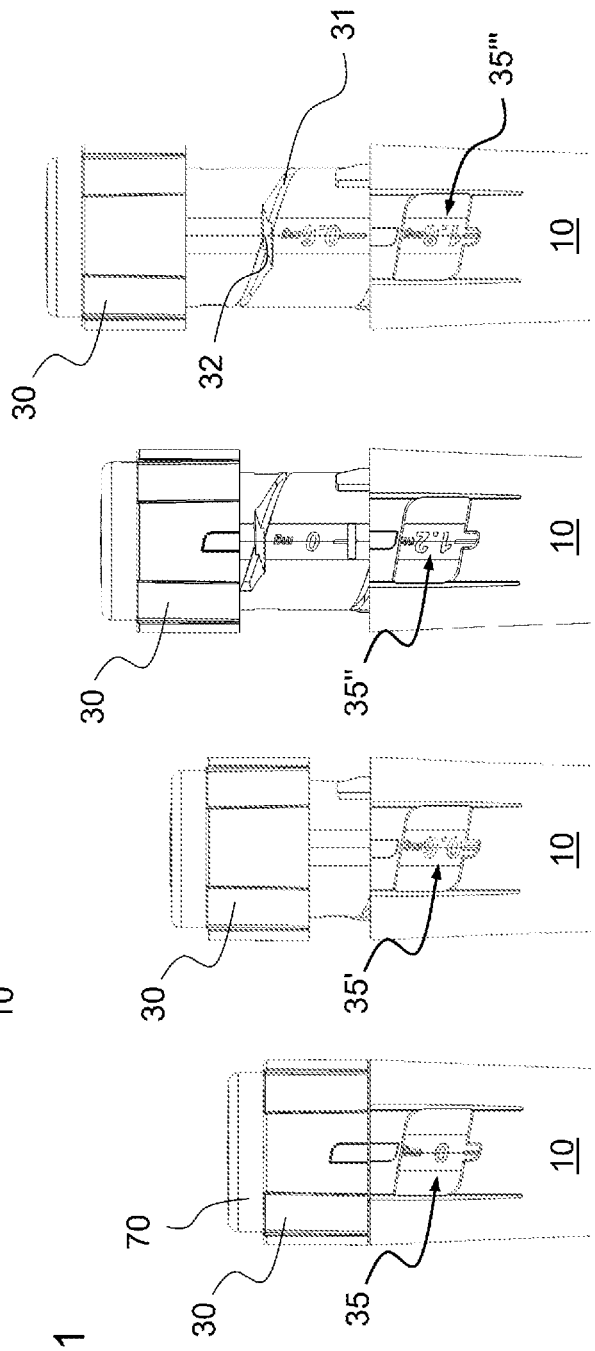
FIG. 1
FIG. 2

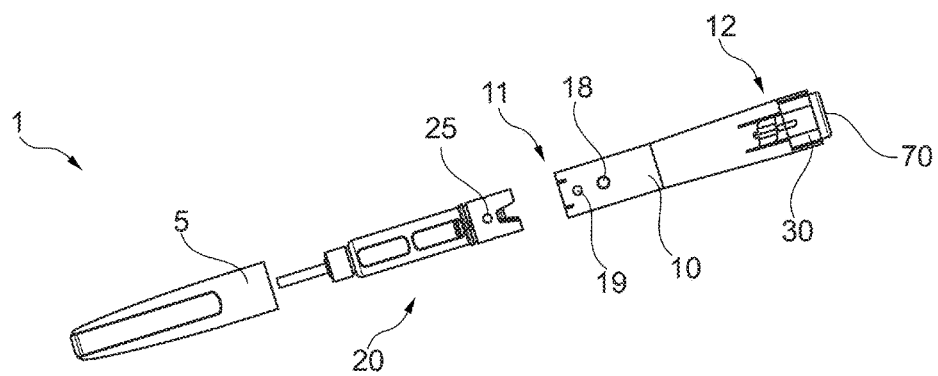
Fig. 3
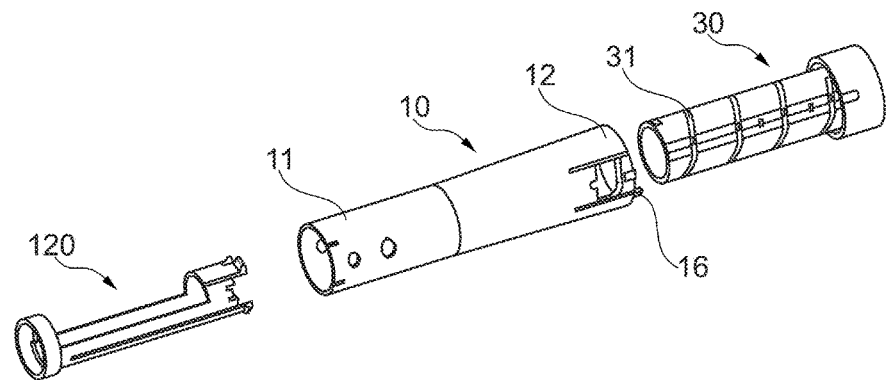
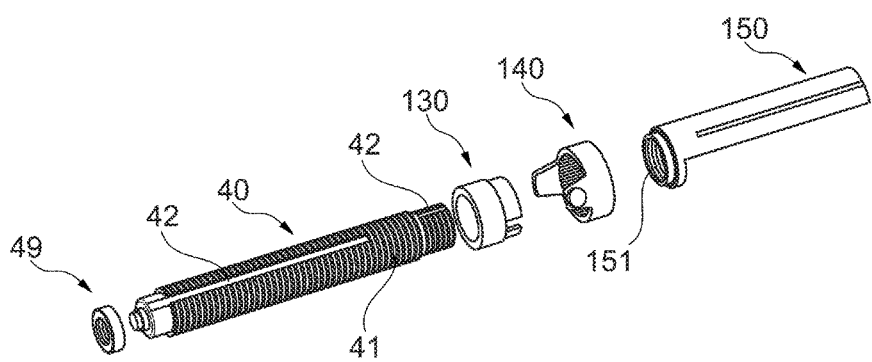
Fig. 4

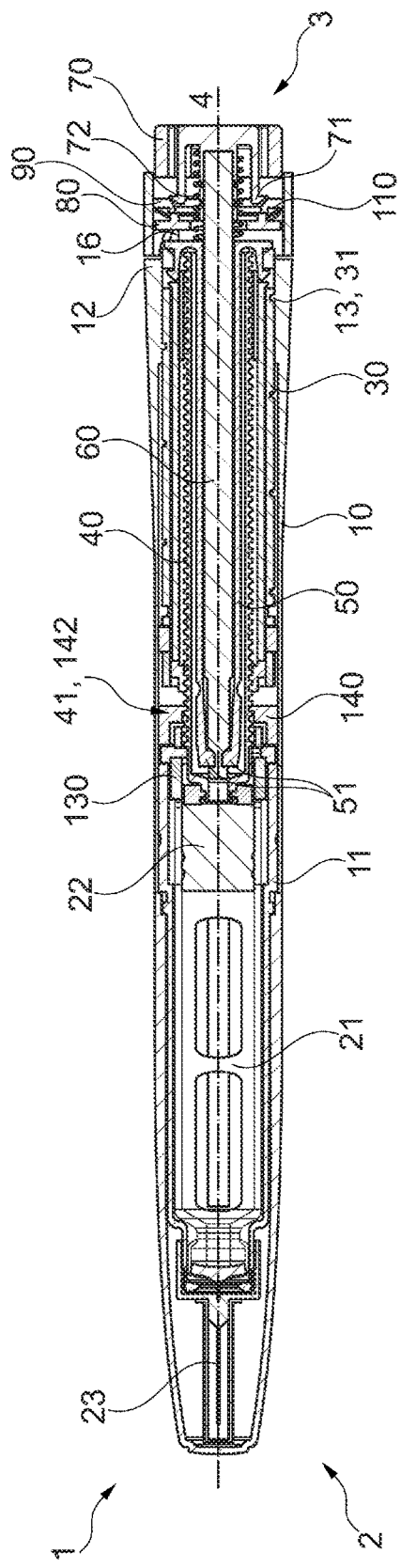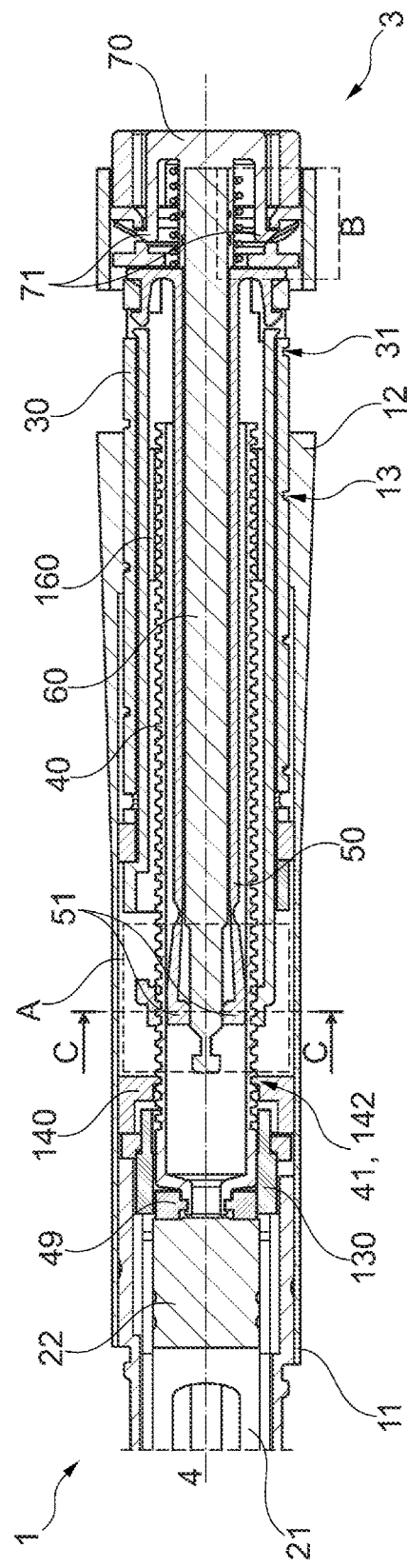

MEDICAMENT DELIVERY DEVICE

TECHNICAL FIELD

The present invention relates to a medicament delivery device, in particular to a medicament delivery device for injecting different and/or multiple doses. More specifically, the present invention relates to a medicament delivery device that allows a user to set a dose to be delivered and that includes a mechanism for ensuring delivery of the entire dose.

BACKGROUND

The present invention relates to auto-injection and/or medicament delivery devices for injecting a dose of medicaments or medicinal substances in fluid form through a needle, such as insulin or hormones. Medicaments or medicinal substances may summarily be referred to as medicaments in the context of the present invention.

Auto-injectors, which are sometimes also referred to as pen-injectors, have been on the market for many years. One of the first auto-injectors was developed for war-times. The main concern was to have the medicament injected as fast as possible without much concern for the patient or for handling aspects. During recent years, some medicaments have been developed that have to be injected by the patients themselves. Therefore, depending on the intended use and type of medicament, injection devices having a varying degree of automatic functions have been developed to facilitate injection of medicaments in a reliable and safe manner for patients and even for trained personnel; e.g. physicians, nurses, etc.

Depending on the medicament or medicinal substance to be injected, it may be beneficial for such medicament delivery devices to allow a user to set the dose to be delivered before injection. This may be achieved by allowing the user to define the volume of fluid that is to be ejected during dose delivery.

There is an ongoing need to provide this type of devices with mechanisms that are easy to assemble during manufacture and reliable in operation. In particular, there is an ongoing need for devices that function reliably even when inappropriately operated by the user.

In view of the above, it is an object of the present invention to provide a device that is easy to assemble during manufacture.

It is a further object of the present invention to provide a device that ensures reliable operation. In particular, it is an object of the present invention to provide a device that functions reliably even when inappropriately operated.

SUMMARY

In order to achieve one or several of the above-mentioned objects, an injection device according to independent claim 1 is provided. Further aspects, improvements and variations are disclosed in the dependent claims, the figures and the description.

According to a first aspect, the present invention relates to a medicament delivery device, preferably a medicament delivery device that allows for delivery or several subsequent doses. Such device may also be referred to as a "multi-dose" medicament delivery device in the context of the present invention. The medicament delivery device preferably allows a user to vary the volume of each dose to be delivered. For example, the device may be configured to allow the user to deliver doses of 0.1 ml, 0.2 ml and/or 0.3 ml.

The device preferably has a device front end, a device back end, and a central longitudinal axis that may extend from the front end to the back end. In the present application, the term "front" refers to the direction pointing to a dose delivery site. When the term "front" part/end is used, this refers to the part/end of the delivery device, or the parts/ends of the members thereof, which is/are located closest to the dose delivery site. The term "front" may also be replaced by "proximal". Correspondingly, the term "back" refers to the direction pointing away from the dose delivery site. When the term "back" part/end is used, this refers to the part/end of the delivery device, or the parts/ends of the members thereof, which is/are located furthest away from the dose delivery site. The term "back" may also be replaced by "distal" or "rear".

The device of the present invention comprises a housing having a housing front end and a housing back end, and a medicament container assembly. The medicament container assembly preferably is configured for accommodating a medicament container with a stopper that is sealingly and slidably arranged inside the container. The medicament container may, for example, have a volume of at least 1 ml, at least 2 ml, 10 ml or less, or 5 ml or less. The medicament container assembly may further include a needle.

The device of the present invention may further include a dose setting element, which may be provided as a dose drum. The dose drum may have a front end and a back end as well as a through hole extending from the back to the front end. It may have a substantially cylindrical shape. The housing back end may be open to allow insertion of the dose drum into the housing back end during assembly of the device.

The dose drum may be axially movable with respect to the housing in a backward direction from an initial position to at least one dosing position (e.g., when rotated in a first direction) in order to set the dose to be delivered. For example, the dose drum may be axially movable with respect to the housing in the backward direction to at least two or at least three different predetermined dosing positions, each dosing position corresponding to a predetermined dose to be delivered. The device may comprise an indication means for indicating the respective dose to a user. The indication means may be provided, for example, by one or several markings on the outer surface of the dose drum. The housing may be provided with at least one window through which the one or several markings are visible to the user.

Furthermore, the dose drum may be axially movable with respect to the housing in a forward direction from the dosing position back to the initial position (e.g., when rotated in a second, opposite direction) in order to deliver the dose set. The dose drum may, for example, be supported in the housing via a threaded connection. For example, a first threading component may be provided along an outer surface of the does drum that engages with a second threading component provided along the inner surface of the housing. Moving the dose drum in the backward direction preferably increases the dose to be delivered.

The device may provide an audible and/or tactile feedback when a predetermined dose setting has been reached. Such feedback may be achieved, for example, by providing the threaded connection with a varying pitch, preferably with a pitch that is different at locations corresponding to the predetermined dose setting/s. For example, the pitch of the first threading component provided along the outer surface of the does drum may be different at locations corresponding to one or several predetermined dose settings.

The device according to the invention preferably allows the user to move the dose drum in the backward and forward directions (e.g., by rotation of the dose drum in the housing) until the desired dose has been set.

The device may further include a plunger rod that may be operationally associated with the stopper. The plunger rod may be supported in the housing via a threaded connection that may be configured to axially guide the plunger rod toward the device front end when the plunger rod is rotated. Preferably, the plunger rod is moved toward the device front when it is rotated in the second direction. The plunger rod may be hollow and/or may be provided with an open back end. The plunger rod may extend in and/or be at least partially surrounded by the dose drum.

The device may further include an activation assembly. Triggering the activation assembly may allow the user to start delivery once the dose has been set. Preferably, the activation assembly is operationally associated with the dose drum such that the activation assembly is moved together with the dose drum in the backward direction with respect to the housing (e.g., when the dose drum is rotated in the first direction).

The activation assembly may include a mechanism that provides a mechanical coupling between the dose drum and the plunger rod. The mechanism may be configured to provide said mechanical coupling at the predefined dose settings mentioned above.

The activation assembly may comprise a plunger rod rotator. The plunger rod rotator may be mechanically coupled to the dose drum such that it is rotated therewith. For example, the plunger rod rotator may be connected to the dose drum in a form-locking manner, preferably by a snap-fit engagement.

The plunger rod rotator may have at least one first deflecting member (e.g., two first deflecting members). The deflecting member/s may be provided as one, two or several arms that, for example, could extend from a front end of the plunger rod rotator. These one or several arms could also be referred to as ratchet arms in the context of the present invention. The plunger rod rotator may thus also be referred to as a ratchet arm drum in the context of the present invention. The plunger rod rotator may extend in and/or be at least partially surrounded by the plunger rod. The plunger rod rotator may also extend in and/or be at least partially surrounded by the dose drum.

The activation assembly may further comprise an activator element that may be movable (e.g., axially) with respect to the plunger rod rotator from an uncoupling position to a coupling position. Preferably, the activator element is axially slidable with respect to the plunger rod rotator from said uncoupling position to said coupling position. The activator element may be an activator rod. The activator rod may extend in and/or be at least partially surrounded by the plunger rod rotator.

Preferably, the at least one first deflecting member operationally couples the plunger rod rotator with the plunger rod when the activator element is in the coupling position. When such coupling position is reached, the rotation of the dose drum in the second direction from the dosing position to the initial position preferably rotates the plunger rod in said second direction. The rotation of the dose drum from the dosing position to the initial position thus preferably leads to a rotation of the plunger rod in the second direction, thereby moving the plunger rod with the stopper towards the device front end.

Preferably, the activator element (i.e., in particular, the activator rod) deflects the first deflecting member of the plunger rod rotator into a position in which said first deflecting member provides for a mechanical coupling of the plunger rod rotator to the plunger rod. The plunger rod may be provided, for example, with at least one first engagement feature along an inner diameter portion thereof that may be configured to engage with at least one second engagement feature provided to the at least one first deflecting member.

The plunger rod preferably is provided with at least two first engagement features that may be offset with respect to each other by approximately 180°. Each first engagement feature may be formed as a tooth provided along an inner diameter portion of the plunger rod. Preferably, each of the first deflecting members is provided with at least one second engagement feature. The second engagement features on the first deflecting members may be offset by approximately 180°. Each second engagement feature may be provided as an external tooth. The first and second engagement features of the plunger rod and the plunger rod rotator, respectively, may be configured to be in an engaged meshing position with respect to one another when the dose drum is in a position corresponding to a predetermined dose setting. The first and second engagement features may be configured to be in an unmeshed position when the position of the dose drum does not correspond to such predetermined dose setting.

The at least one first deflecting member may, for example, be deflected away from the central longitudinal axis of the device. This may be achieved by axially moving the activator element (in particular, the activator rod) toward the device front end. The activator rod, for example, may comprise at least a first section having a smaller diameter and at least a second section having a larger diameter (with the term diameter being equivalent to the width of the activator rod when its cross sectional shape is not round). When the activator rod is in the uncoupling position, the position of the first section along the longitudinal axis of the device may correspond to that of the at least one first deflecting member. When the activator rod is in the coupling position, the position of the second section along the longitudinal axis of the device may correspond to that of the at least one first deflecting member. The second section of larger diameter may thus spread the at least one first deflecting member away from the central longitudinal axis. A ramped transition section may be provided between said first and second sections to provide for a smooth movement of the activator rod.

The plunger rod may be provided with an outer threading along an outer surface thereof. This outer threading may engage with an inner threading provided in the housing and/or a further element that connected thereto. For example, the outer threading may engage with the inner threading of a threaded insert. The threaded insert may be located in and connected to the housing in a rotationally and/or axially fixed manner. For example, the threaded insert may be connected to the housing in a form-locking manner, preferably by a snap-fit engagement of corresponding locking features (e.g., the threaded insert comprises a locking feature that engages with a recess or opening of the housing when the device is assembled).

The device may include a back rotation blocking mechanism that inhibits rotation of the plunger rod in the first direction. The back rotation blocking mechanism may be a ratchet mechanism. The back rotation blocking mechanism, for example, may inhibit rotation of the plunger rod in the first direction when the dose drum is rotated in said first direction. It may thus prevent rotation of the plunger holder in said first direction with the dose drum. Alternatively or additionally, once the activation assembly is triggered, the back rotation blocking mechanism may inhibit rotation of the dose drum in the first direction until the dose drum reaches its initial position again. The ratchet mechanism may include a first element with a ratchet pawl that engages with teeth of a second element.

The device may comprise, for example, a back rotating blocker element. The back rotating blocker element may be connected to the plunger rod in a rotationally fixed manner. For example, the plunger rod may include a first locking feature (e.g. a channel or a protrusion) along a front portion thereof that engages with a corresponding locking feature of the back rotating blocker element (e.g. a protrusion or a channel). The plunger rod may be at least partially surrounded by the back rotating blocker element and/or by the threaded insert.

The back rotating blocker element may be provided with the ratchet pawl. The ratchet teeth may be provided, for example, on the threaded insert. The back rotating blocker element and the threaded insert may thus together form the ratchet mechanism.

The device may comprise at least one second deflecting member. The at least one second deflecting member may be configured to lock the position of the activator element with respect to the plunger rod rotator in the coupling position when the activation assembly is triggered by moving the activator element (in particular, the activator rod) from the uncoupling position to said coupling position. Preferably, the activator element is unlocked when the dose drum reaches its initial position again. The at least one second deflecting member may be a hooked lever.

The at least one second deflecting member may be configured to lock the axial position of the activator element with respect to the plunger rod rotator in the coupling position by mechanically engaging a portion of the dose drum and/or a portion of the plunger rod rotator. Preferably, the at least one second deflecting member may be configured to lock the axial position of the activator element with respect to the plunger rod rotator in the coupling position by mechanically engaging a separate additional locking element. This locking element may be arranged, for example, in a back end portion of the dose drum. The locking element may be connected to the dose drum such that a movement of the locking element with respect to the dose drum in the axially rearward direction is limited and/or prevented. The locking element may be, for example, a lock ring.

The activation assembly may comprise, for example, a dose activator, which may be provided as a dose activator button or slider. The dose activator button may be fixedly connected to the activator element (in particular, the activator rod) and/or to the at least one second deflecting member. For example, the at least one second deflecting member may be integrally formed with the dose activator button. Preferably, the dose activator button comprises at least two second deflecting members, which may be formed by at least two hooked deflecting arms.

The dose activator button may be axially movable with respect to the dose drum. For example, the dose activator button may be axially movable with respect to the dose drum from a first position corresponding to the uncoupling position of the activator element to a second position corresponding to the coupled position of the activator element.

The dose activator button may be configured to be operated by the user's hand. Preferably, the dose activator button is operable by a user's finger.

The activation assembly may further comprise, a release spring. The dose activator button may be movable against an output axial force of said release spring from its first position to its second position and/or may be axially movable by the output axial force of said release spring from its second position to its first position. When the dose drum is in the dosing position and the dose activator button is moved to the second position, the at least one second deflecting member preferably inhibits the dose activator button from being moved to the first position by the output axial force of the release spring, thereby locking the activator element in the coupling position with respect to the plunger rod rotator.

The activation assembly may further comprise an unlocking element. The unlocking element may be configured to disengage the at least one second deflecting member to unlock the activator element when the dose drum reaches the initial position again. For example, the unlocking element may be configured to disengage the at least one second deflecting member from the locking element. To facilitate disengagement, the unlocking element and/or the at least one second deflecting member may have a ramped surface. This ramped surface may be configured to deflect the at least one second deflecting member towards or away from the central longitudinal axis.

The unlocking element preferably is axially movable with respect to the dose drum, with respect to the dose activator button and/or with respect to the locking element. For example, the unlocking element may be configured to be pressed in the backward direction against the at least one second deflecting member (e.g., when the dose drum reaches its initial position). The activation assembly may include, for example, a spring or washer (e.g., a disk spring), wherein the unlocking element is movable in the backward direction with respect to the dose drum, the dose activator button and/or the locking element against an output axial force of said spring or washer. The spring or washer may be arranged, for example, between the unlocking element and the locking element of the activation assembly. The unlocking element and/or the spring may be arranged in a back end portion of the dose drum. The unlocking element may be a slider ring.

The housing may comprise at least one tab that is configured to press the unlocking element in the backward direction when the dose drum reaches its initial position. Preferably, the housing comprises at least two tabs.

The device may further include a mechanism to avoid movement of the plunger rod towards the device front end once the plunger rod has been moved axially forward with respect to the medicament container assembly by a predetermined distance. This distance may correspond to a maximum extent to which the stopper should be moved in the axially forward direction with respect to the medicament container (i.e. a position in which a predetermined maximum medicament volume has been delivered by the device).

The device may, for example, comprise a dosing stop element that is operationally associated with the plunger rod via a threaded connection. The dosing stop element may be axially movable with respect to the plunger rod. Alternatively or additionally, the dosing stop element may be axially movable and/or rotationally fixed with respect to the dose drum. The dosing stop element may be configured to abut the plunger rod, an additional end stop element connected to the plunger rod in a rotationally fixed manner, the housing and/or an additional element connected to the housing when the plunger rod has been moved axially forward with respect to the medicament container assembly by the predetermined distance.

The dose drum, the plunger rod, the plunger rod rotator, and the activator rod may form a sub-assembly that is configured to be pre-assembled before insertion into the housing. The sub-assembly further includes at least one or all of the following elements: the dose activator button, the back rotating blocker element, the threaded insert, the dose stop. Such sub-assembly may simplify the assembly of the device. The sub-assembly may form a rear assembly with the housing.

BRIEF DESCRIPTION OF THE FIGURES

The invention will be described in more detail with reference to the figures below. These schematic figures disclose an embodiment of the invention for illustrational purposes only. In particular, the disclosure provided by the figures is not meant to limit the scope of protection conferred by the invention. The figures show:

FIG. 1 a perspective view of a medicament delivery device according to a preferred embodiment of the invention;

FIG. 2 different side views of the back end of the device according to the preferred embodiment of FIG. 1 with a dose drum being shown in different predetermined dosing positions;

FIG. 3 a side view of the device according to the preferred embodiment of FIG. 1 with a rear assembly, a medicament container assembly and a cap being exploded;

FIG. 4 an exploded perspective view of some elements of the rear assembly of the device according to the preferred embodiment of FIG. 1;

FIG. 6 a cross-sectional side view of the device according to the preferred embodiment of FIG. 1;

FIG. 7 a cross-sectional side view of the device according to the preferred embodiment of FIG. 1 with the dose drum in a predetermined dosing position and the activation assembly being triggered;

DETAILED DESCRIPTION

Figure 5:
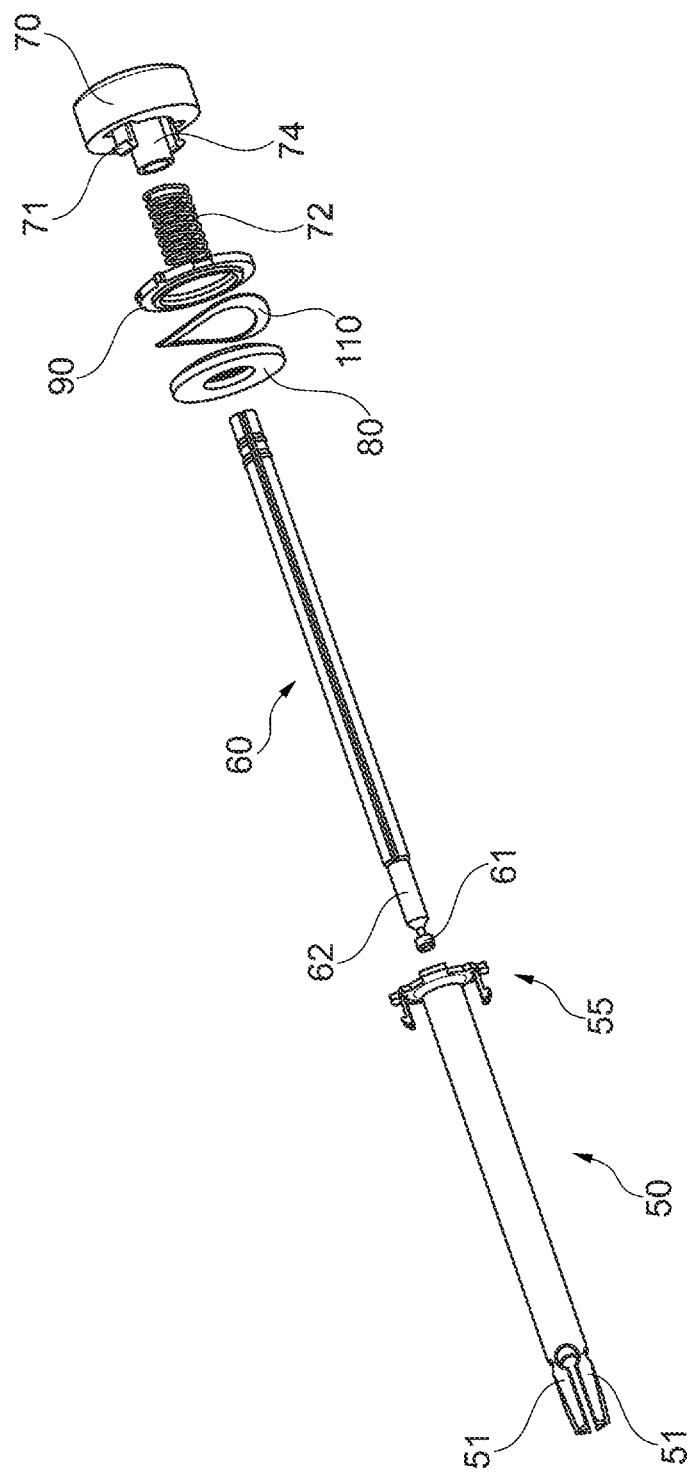
FIG. 5 an exploded perspective view of the activation assembly of the device according to the preferred embodiment of FIG. 1.
Figure 8:
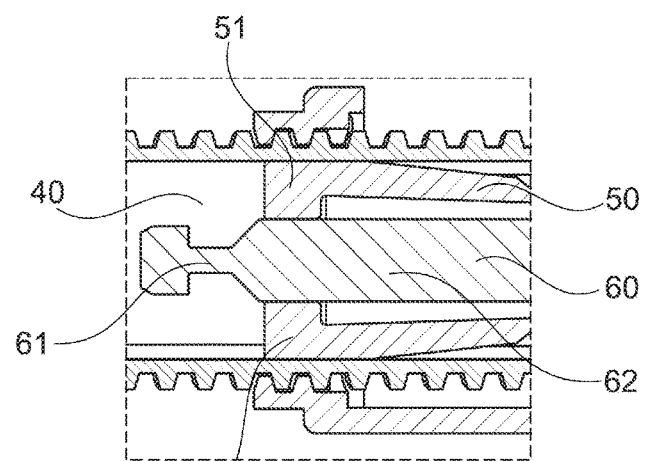
FIG. 8 the detail A of FIG. 7.

FIG. 1 illustrates a device 1 according to an exemplary embodiment of the invention with a dose drum 30 in an initial position. As shown, the device has a device front end 2, a device back end 3 and a central longitudinal axis 4 extending therebetween. The device comprises a cap 5 and a housing 10 with a window 14 through which dose markings 35 of the dose drum 30 can be seen. As will also be appreciated, the device comprises a dose activator button 70 that in this exemplary embodiment is provided at the device back end 3.

FIG. 2 illustrates the device 1 of FIG. 1 with the dose drum 30 in different predetermined dosing positions, as indicated by the different markings 35, 35', 35" and 35'". As will be appreciated, the dose drum 30 can be moved by a user with respect to the housing 10 in the backward direction from the initial position shown on the left hand side in FIG. 2 to the different dosing positions. In the exemplary embodiment of the figures, this backward movement is achieved by rotating the dose drum 30 in a first direction along an outer threading 31 provided on its outer surface. This outer threading 31 together with an inner threading 13 provided in the housing (see FIG. 6) may provide a threaded connection by which the dose drum 30 is supported in the housing 10.

Optionally, the dose drum 30 may be moved backward and forward without effecting medicament delivery as long as an activation assembly that will be described in more detail below is not triggered. In the illustrated embodiment, the activation assembly may be triggered by depressing the activator button 70.

As mentioned above, the device may be configured to provide an audible and/or tactile feedback to the user when a predetermined dosing position is reached. In the illustrated exemplary embodiment this is achieved by providing the threading 31 with a different pitch at locations 32.

Figure 11:
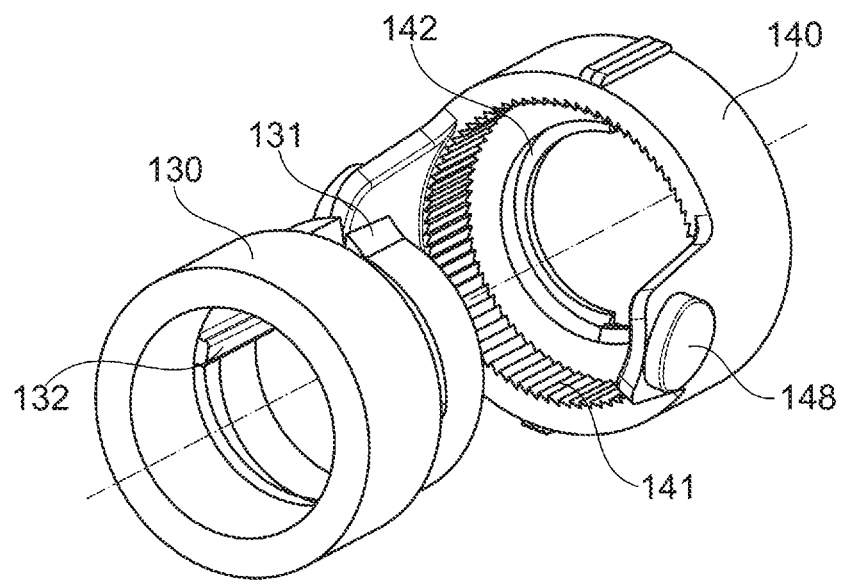
FIG. 11 an enlarged exploded perspective view of the back rotating blocker element and the threaded insert.

FIG. 3 shows a side view of the device 1 with a rear assembly (including the housing 10, the dose drum 30 and the dose activator button 70), a medicament container assembly 20, and the cap 5 being exploded. As shown, the entire mechanism of the device may be pre-assembled in the housing 10 before inserting the medicament container assembly 20 into the hosing from a housing front end 11. Furthermore, the mechanism may be pre-assembled as a sub assembly that is then inserted into the housing (e.g. from a housing back end 12). In this context, the sub-assembly may be fixedly attached to the housing by a snap-fit engagement of a locking feature 148 of a threaded insert 140 (see FIG. 11) that engages into a first opening 18 of the housing 10.

The medicament container assembly 20 may include a locking feature 25 that fixedly attaches said medicament container assembly 20 to the housing 10 by engaging a second opening 19. As shown in more detail in the cross-section of FIG. 6, the medicament container assembly 20 may include a medicament container 21, a stopper 22, and a needle 23 that is attached to the container's front end. The stopper 22 may be slidably arranged in the medicament container 21. A plunger rod 40 may be operationally associated with the stopper 22 in order to move the stopper towards the front end of the container 21 and thereby deliver the medicament. The plunger rod 40 may be coupled to the stopper 22 via a spinner 49 that is rotatable with respect to the plunger rod and/or with respect to the stopper 22.

FIG. 4 illustrates different components that form part of the rear assembly of FIG. 3. Apart from the housing 10, the dose drum 30 and the plunger rod 40 with the spinner 49, the rear assembly may include a back rotating blocker element 130, the above-mentioned threaded insert 140, a sliding drum 120, and a dosing stop element 150.

FIG. 5 illustrates the components of the activation assembly, which apart from the dose activator button 70 may include a plunger rod rotator 50, an activator rod 60, a locking element 80, an unlocking element 90, a disk spring 110, and a release spring 72.

The plunger rod rotator 50 may comprise two first deflecting members or arms 51 (e.g., at its front end). The plunger rod rotator 50 may be connected to the dose drum 30 in a rotationally and/or axially fixed manner. For example, the plunger rod rotator 50 may be mechanically engaged to the dose drum 30 (e.g., via a snap-fit connection 55).

The activator rod 60 may comprise a first section 61 having a smaller diameter and a second section 62 having a larger diameter. The first section 61 may be arranged in front of the second section 62. The activator rod 60 may be arranged in and/or partially surrounded by the plunger rod rotator 50. The activator rod may be connected to the dose activator button 70 in an axially fixed manner, for example at its rear end.

The locking element 80 and the unlocking element 90 may be provided by a lock ring 80 and a slider ring 90, respectively. As shown, the lock ring 80 and/or the slider ring 90 may be arranged in a back end portion of the dose drum 30, which may optionally be enlarged.

As described in more detail below, the slider ring 90 preferably is axially movable with respect to the lock ring 80. For example, the slider ring 90 may be axially movable with respect to the lock ring 80 against an output axial force of the disk spring 110. The disk spring 110 may be arranged between the locking element 80 and the unlocking element 90. As the skilled person will recognize, the disk spring 110 may be replaced by other resilient elements.

The release spring 72, the locking element 80 and/or the unlocking element 90 may be at least partially arranged around the activator rod 60 and/or around a protrusion 74 of the dose activator button 70.

FIGS. 6 to 13 illustrate the dose setting, activation and dose delivery sequence for the device according to the exemplary embodiment. More specifically, FIG. 6 shows the device 1 with the dose drum 30 in an initial position and the activator rod 60 in an uncoupling position. In this uncoupling position, the plunger rod rotator 50 is disengaged from the plunger rod 40. The plunger rod rotator's first deflecting arms 51 are retracted. As shown in FIG. 6, the position of the activator rod's smaller diameter section 61 along the central longitudinal axis 4 may generally correspond to the position of said first deflecting arms 51 when the activator rod 60 is arranged in this uncoupling position.

FIG. 7 shows the rear portion of the device 1 in a position in which the dose drum 30 has been moved backwards by rotating the dose drum in a first direction along the threaded connection 13, 31 to a dosing position. The activation assembly may then be triggered by depressing the dose activator button 70 such that the triggered position shown in FIG. 7 is reached. The activator rod 60 is thus axially moved towards the device front end with respect to the plunger rod rotator 50 to a coupling position, whereby the larger diameter section 62 spreads the deflecting arms 51 apart (see also FIG. 8). In particular, the activator rod 60 may be configured to deflect the arms 51 away from the central longitudinal axis 4 when it is moved from the uncoupling to the coupling position.

Figure 9:
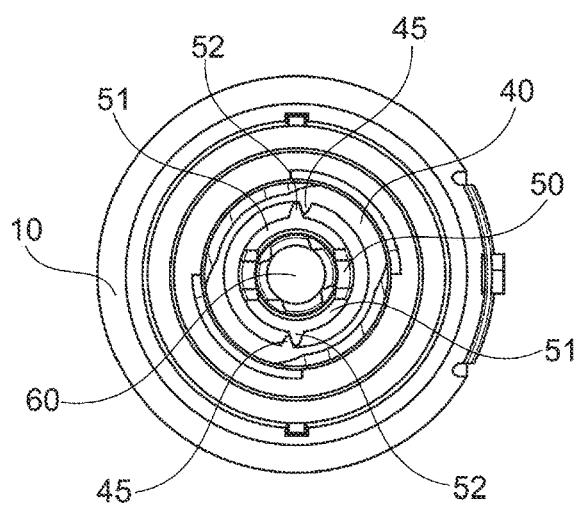
FIG. 9 the cross-section C-C of FIG. 7.

As shown in FIG. 9, this leads to an engagement of one or more first engagement features of the plunger rod (which in the exemplary embodiment of the figures are provided by two inwardly protruding teeth 45) with one or more second engagement features of the first deflecting arms 51 (which in the exemplary embodiment of the figures are provided by two outwardly protruding teeth 52) when the dose drum 30 is in one of the predetermined dosing positions. The first and/or second engagement features may be configured such that the rotation of the dose drum 30 is not transmitted to the plunger rod 40 when the activation mechanism is triggered outside the one or more predetermined dosing positions. For example, even though the activation assembly is triggered, the rotation of the dose drum 30 may not be transmitted to the plunger rod 40 when the dose drum 30 is rotated in the second direction until the next predetermined dosing position is reached. Once the one or more first engagement features of the plunger rod 40 engage the one or more second engagement features of the first deflecting arms 51, the rotation of the dose drum 30 in the second direction will lead to a rotation of the plunger rod 40 via the plunger rod rotator 50.

The plunger rod 40 may be supported in the housing 10 via a threaded connection that may be provided, for example, by an outer threading 41 of the plunger rod and an inner threading 142 of the threaded insert 140. This threaded connection may be configured to axially guide the plunger rod 40 toward the device front end 2 when the plunger rod 40 is rotated in the second direction with the dose drum 30. The stopper 22 may move with the plunger rod toward the device front end 2, thus delivering the medicament from the container 21. The threaded connections 41, 142 and 13, 31 via which the plunger rod 40 and the dose drum 30 are supported in the housing 10, respectively, preferably have a different pitch. For example, the thread pitch of the threaded connection 13, 31 may be greater than that of the threaded connection 41. Since the pitch of the threaded connection 13, 31 may vary at locations 32, FIG. 2, (see above), the pitch of this connection may be measured between these locations 32. Alternatively, an "average" pitch over the entire length of threading 31 could be referred to.

Figure 10:
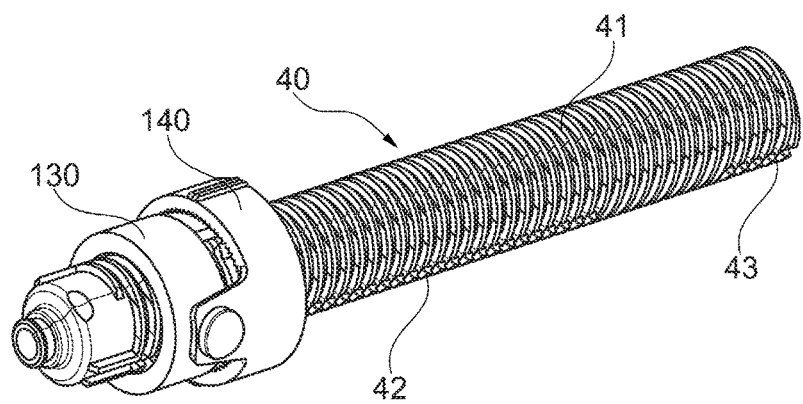
FIG. 10 a perspective view of the plunger rod with the back rotating blocker element and the threaded insert disposed thereon.

As shown in FIGS. 6, 7 and 10, the device 1 may further include a mechanism to avoid a movement of the plunger rod 40 in the axially backward direction. This mechanism may, in particular, be configured to prevent a rotation of the plunger rod 40 in the first direction and may thus also be referred to as a back rotation blocking mechanism in the context of the invention. The back rotation blocking mechanism may include a back rotating blocker element 130 that is connected to the plunger rod 40 in a rotationally fixed manner. For example, the plunger rod 40 may include a channel 42 (e.g., along a front portion thereof; see also FIG. 4) that may engage with a corresponding protrusion 132 of the back rotating blocker element 130.

The back rotating blocker element 130 may provide for a ratchet mechanism together with the housing 10 and/or an element connected thereto. In the exemplary embodiment of the figures, such ratchet mechanism is provided between the back rotating blocker element 130 and the threaded insert 140. For this purpose, the back rotating blocker element 130 may be provided with a pawl 131 that engages with teeth 141 of the threaded insert 140 (see FIG. 11).

The device 1 according to the invention may further include a mechanism to avoid a movement of the plunger rod 40 towards the device front end 2 once the plunger rod 40 has been moved axially forward with respect to the medicament container assembly 20 by a predetermined distance. This distance may correspond to a maximum extent to which the stopper 22 should be moved in the axially forward direction with respect to the medicament container 21 (i.e. the position in which a predetermined maximum medicament volume has been delivered by the device 1). For example, the device 1 may include a dosing stop element 150 that may be operationally associated with the plunger rod 40 via a threaded connection. In particular, the dosing stop element 150 may comprise an inner threading 151 (see FIG. 4) via which it is engaged to the outer threading 41 of the plunger rod.

The dosing stop element 150 may be axially movable with respect to the plunger rod 40, the dose drum 30 and/or the housing. In addition, the dosing stop element 150 may be connected in a rotationally fixed manner to the dose drum 30, for example via the sliding drum 120. In particular, the dosing stop element 150 may be configured to be rotated with the dose drum 30 when the dose drum 30 is rotated in the first direction in order to set the dose to be delivered. This may lead to the dose stop element 150 being moved in the backward direction with respect to the plunger rod 40 during setting of the dose. When the dose drum 30 is rotated in the second direction, the dose stop element 150 may move forward together with the plunger rod 40, for example when the plunger rod 40 is rotated in said second direction together with the dose drum 30.

The dose stop element 150 may thus be configured to move further in the backward direction each time a dose is set and delivered. In view of the different pitches of the threaded connections 13, 31 and 41, 142 such arrangement may lead to a successive movement of the dosing stop element in the axially backward direction with respect to the housing 10, with respect to the dose drum 30 and/or with respect to the plunger rod 40 when the plunger rod 40 is rotated in the second direction. The dosing stop element 150 may be configured to abut the housing 10, the plunger rod 40 and or an element that is connected thereto in an axially fixed manner when the predetermined maximum medicament volume has been delivered. For example, the dosing stop element 150 may be configured to abut an end stop element 160 (see FIG. 7). The end stop element 160 may be rotationally and/or axially fixed to the plunger rod 40, e.g., via a protrusion that extends into a second channel 43 of the plunger rod 40, FIG. 10.

Figure 12:
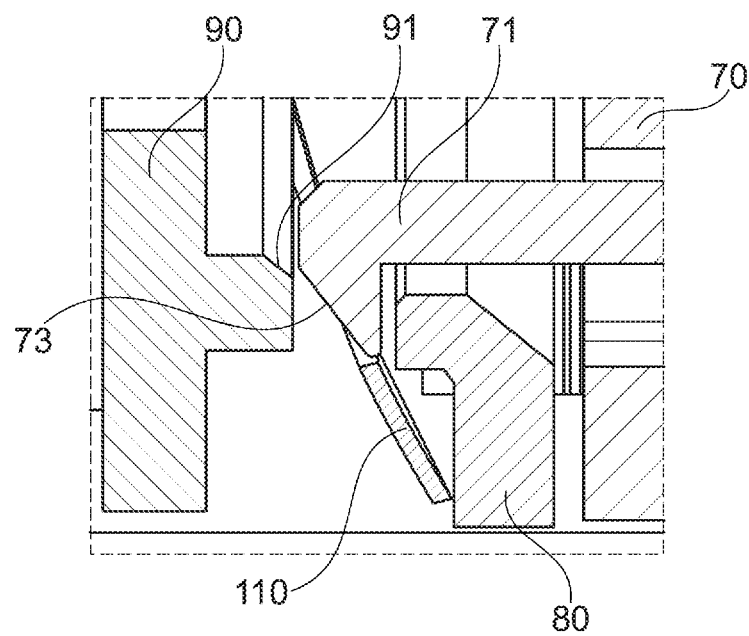
FIG. 12 the detail B of FIG. 7.
Figure 13A:
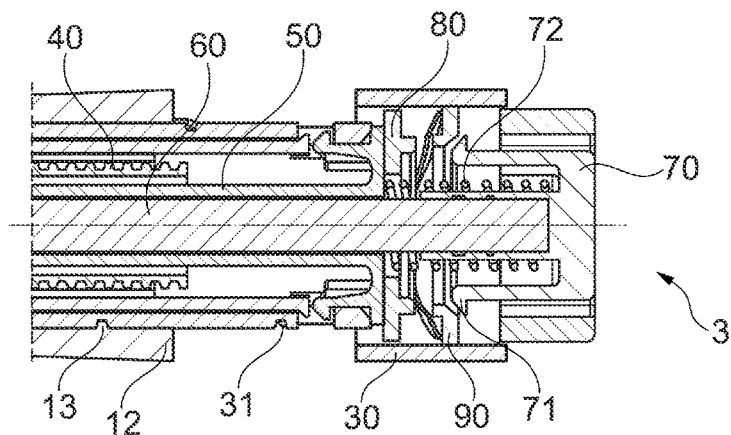
FIG. 13A a cross-sectional side view illustrating a dose activator button of the device according to the preferred embodiment of FIG. 1 in an unlocked position before the activation assembly is triggered.

FIGS. 12 and 13 illustrate the locking of the activator rod 60 in the coupling position. As shown, at least one second deflecting member 71 (in the exemplary embodiment of the figures two hooked arms of the dose activator button 70) may lock the axial position of the activator rod 60 with respect to the dose drum 30 when the activation assembly is triggered. For example, the second deflecting member 71 may engage the lock ring 80, thereby fixing the axial position of the dose activator button 70 with respect to the dose drum 30, as shown in the cross section of FIG. 13A and the detail of FIG. 12.

Figure 13B:
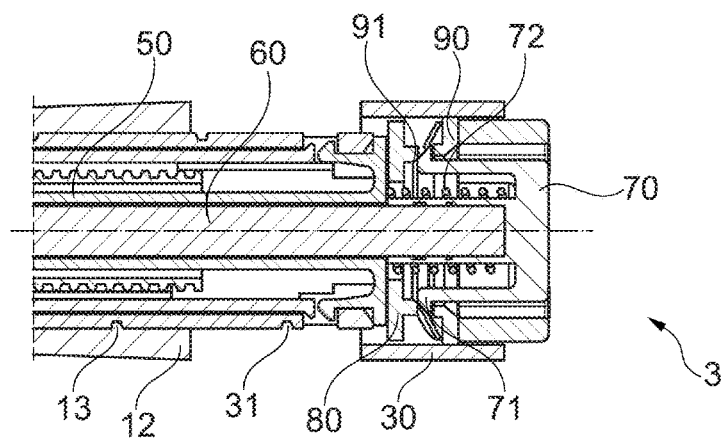
FIG. 13B a cross-sectional side view illustrating the dose activator button in a locked position after triggering of the activation assembly.
Figure 13C:
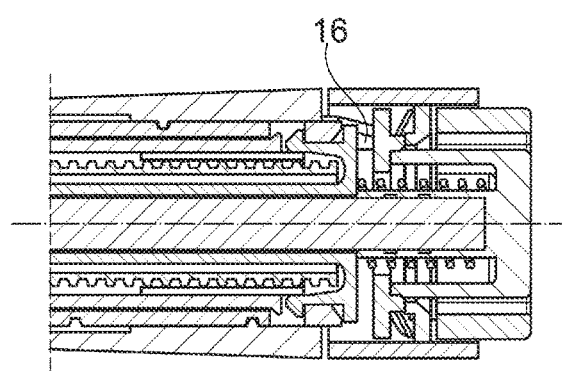
FIG. 13C a cross-sectional side view illustrating the dose activator button while being released upon return of the dose drum to an initial position.

As illustrated by the sequence of FIGS. 13A to 13C, the at least one second deflecting member 71 may be configured to be disengaged when the dose drum is moved towards the device front end for a predetermined distance. In particular, the second deflecting member 71 may be configured to be disengaged once the dose set with the dose drum 30 has been delivered, for example by rotating the dose drum 30 in the second direction from the dosing position shown in FIG. 13B back to the initial position shown in FIG. 13C.

In the exemplary embodiment of the figures, the slider ring 90 is used to disengage the at least one second deflecting member 71 from the lock ring 80. For example, the slider ring 90 and/or the at least one second deflecting member 71 may be provided with ramped surfaces 91 and 73, respectively, that urge the at least one second deflecting member 71 toward the central longitudinal axis 4 of the device 1 when the slider ring 90 is moved axially backward with respect to the lock ring 80. When the dose drum 30 reaches again the initial position shown in FIG. 13C, the slider ring 90 may, for example, be urged axially backward with respect to the lock ring 80 against an output axial force of the disk spring 110 by an abutment with one or several housing tabs 16. Once the at least one second deflecting member 71 is disengaged from the lock ring 80, the dose activator button 70 with the activator rod 60 connected thereto may be moved back to the uncoupling position by an output axial force of the release spring 72. It is thus ensured that the entire dose is delivered before a new dose can be set.

The output axial force of the disk spring 110 may subsequently return the slider ring 90 to the position shown in FIGS. 13A and 13B when the next dose is being set by moving the dose drum 30 in the backward direction with respect to the housing 10.

In view of the above, the present invention provides a device that is easy to assemble during manufacture and, at the same time, functions reliably even when inappropriately operated by the user.

While aspects of the invention are illustrated and described in detail in the figures and in the foregoing description, such illustration and description is to be considered illustrative or exemplary and not restrictive. Also, reference signs in the claims should not be construed as limiting the scope.

It will also be understood that changes and modifications may be made by those of ordinary skill within the scope and spirit of the following claims. In particular, the present invention covers further embodiments with any combination of features from different embodiments described above. It is also to be noted in this context that the invention covers all further features shown in the figures individually, although they may not have been described individually in the foregoing description.

Whenever the word "comprising" is used in the claims, it should not be construed to exclude other elements or steps. Similarly, the indefinite article "a" or "an" does not exclude a plurality. A single unit may fulfill the functions of several features recited in the claims. It should also be understood that the terms "essentially", "substantially", "about", "approximately" and the like used in connection with an attribute or a value may define the attribute or the value in an exact manner in the context of the present disclosure. The terms "essentially", "substantially", "about", "approximately" and the like could thus also be omitted when referring to the respective attribute or value.

The invention claimed is:

1. A multi-dose medicament delivery device comprising:
a device front end;
a device back end;
a central longitudinal axis;
a housing having a housing front end and a housing back end;
a medicament container assembly, the medicament container assembly being configured for accommodating a medicament container with a stopper;
a dose drum that is supported in the housing via a first threaded connection;
  wherein the dose drum is axially movable with respect to the housing in a backward direction from an initial position to at least one dosing position when rotated in a first direction in order to set a dose to be delivered; and
  wherein the dose drum is axially movable with respect to the housing in a forward direction from the dosing position to the initial position when rotated in a second, opposite direction in order to deliver the dose set;

a plunger rod that is operationally associated with the stopper and supported in the housing via a second threaded connection, wherein the threaded connection is configured to axially guide the plunger rod toward the device front end when the plunger rod is rotated in the second direction, where the plunger rod has an inner surface with an inwardly radial protruding tooth corresponding to a predetermined dosing position; and an activation assembly comprising:
a plunger rod rotator that is coupled to the dose drum and has at least one first deflecting member comprising an outwardly radial protruding tooth;
an activator rod that is axially movable with respect to the plunger rod rotator from an uncoupling position to a coupling position, wherein, when the activator rod is in the coupling position and the dose drum is rotated in the second direction from the dosing position the plunger rod does not rotate until the outwardly radial protruding tooth of the at least one first deflecting member engages the inwardly radial protrusion; and
at least one second deflecting member that is configured to lock the activator rod with respect to the plunger rod rotator in the coupling position until the dose drum reaches the initial position again.

2. The device according to claim 1, wherein the at least one first deflecting member is deflected away from the central longitudinal axis by axially moving the activator rod towards the device front end.

3. The device according to claim 1, wherein the plunger rod rotator comprises at least two first deflecting members.

4. The device according to claim 1,
wherein the plunger rod is provided with at least one first engagement feature along an inner diameter portion thereof;
wherein the at least one first deflecting member is provided with at least one second engagement feature; and
wherein the at least one first engagement feature is configured to be engaged with the at least one second engagement feature when the plunger rod rotator is operationally coupled with the plunger rod.

5. The device according to claim 1, wherein the activation assembly further comprises a dose activator element, wherein the dose activator element is fixedly connected to the activator rod and to the at least one second deflecting member.

6. The device according to claim 5,
wherein the activation assembly further comprises a release spring;
wherein the dose activator element is movable against an output axial force of the release spring from a first position to a second position;
wherein the dose activator element is movable by the output axial force of the release spring from the second position to the first position; and
wherein, when the dose drum is in the dosing position and the dose activator element is moved to the second position, the at least one second deflecting member inhibits the dose activator element from being moved from the second position into the first position by the output axial force of the release spring until the dose drum reaches the initial position again.

7. The device according to claim 1, wherein the activation assembly comprises a locking element and an unlocking element that are both separately positioned with housing such that the activator rod moves relative to both the locking element and the unlocking element when the activator rod moves from the uncoupling position to the coupling position;
wherein the at least one second deflecting member is configured to lock the axial position of the activator rod with respect to the plunger rod rotator in the coupling position by mechanically engaging with the locking element; and
wherein the unlocking element is configured to disengage the at least one second deflecting member from the locking element.

8. The device according to claim 7, wherein the unlocking element and/or the at least one second deflecting member has a ramped surface, wherein the ramped surface is configured to deflect the at least one second deflecting member towards or away from the central longitudinal axis.

9. The device according to claim 7, wherein the unlocking element is axially movable with respect to the dose drum.

10. The device according to claim 7, wherein the unlocking element is configured to be pressed in the backward direction against the at least one second deflecting member when the dose drum reaches its initial position.

11. The device according to claim 1, wherein the device includes a ratchet mechanism that inhibits rotation of the plunger rod in the first direction.

12. The device according to claim 11, wherein the device comprises a back rotating blocker element and a threaded insert;
wherein the back rotating blocker element is connected to the plunger rod in a rotationally fixed manner; and
wherein the back rotating blocker element and the threaded insert together form the ratchet mechanism.

13. The device according to claim 1, wherein the activation assembly is operationally associated with the dose drum such that the activation assembly is moved together with the dose drum in the backward direction with respect to the housing when the dose drum is rotated in the first direction.

14. The device according to claim 1,
wherein the dose drum is axially movable with respect to the housing in the backward direction to at least two or at least three different predetermined dosing positions, each dosing position corresponding to a predetermined dose to be delivered;
wherein the device comprises an indication means for indicating the respective dose.

15. The device according to claim 1, wherein the activation arrangement further comprises a dosing stop element that is operationally associated with the plunger rod via a threaded connection, the dosing stop element being axially movable with respect to the plunger rod and configured to abut the plunger rod and/or an end stop element connected to said plunger rod in a rotationally fixed manner when the plunger rod has been moved axially forward with respect to the medicament container assembly by a predetermined distance.

16. The device according to claim 5, wherein the dose drum, the plunger rod, the plunger rod rotator, the activator rod, and the dose activator element form a sub-assembly that is configured to be pre-assembled before insertion into the housing.

17. A multi-dose medicament delivery device comprising:
a device front end;
a device back end;
a central longitudinal axis;
a housing having a housing front end and a housing back end;

a medicament container assembly, the medicament container assembly being configured for accommodating a medicament container with a stopper;

a dose drum that is supported in the housing via a first threaded connection;
  wherein the dose drum is axially movable with respect to the housing in a backward direction from an initial position to at least one dosing position when rotated in a first direction in order to set a dose to be delivered; and
  wherein the dose drum is axially movable with respect to the housing in a forward direction from the dosing position to the initial position when rotated in a second, opposite direction in order to deliver the dose set;

a plunger rod that is operationally associated with the stopper and supported in the housing via a second threaded connection, wherein the threaded connection is configured to axially guide the plunger rod toward the device front end when the plunger rod is rotated in the second direction; and an activation assembly comprising:
  a dose activator button;
  a locking ring;
  a plunger rod rotator that is coupled to the dose drum and has at least one first deflecting member;
  an activator rod that is axially movable with respect to the plunger rod rotator from an uncoupling position to a coupling position, wherein, when the activator rod is in the coupling position, the at least one first deflecting member operationally couples the plunger rod rotator with the plunger rod such that the rotation of the dose drum in the second direction from the dosing position to the initial position rotates the plunger rod in said second direction; and
  where the dose activator button comprising a second deflecting member that engages the locking ring to axially lock the activator rod with respect to the dose drum when the rod rotator is in the coupling position.

* * * * *